United States Patent
Yaniv et al.

(10) Patent No.: US 10,624,841 B2
(45) Date of Patent: Apr. 21, 2020

(54) NANOBUBBLER

(71) Applicants: Zvi Yaniv, Austin, TX (US); Igor Alexander Goldman, Austin, TX (US)

(72) Inventors: Zvi Yaniv, Austin, TX (US); Igor Alexander Goldman, Austin, TX (US)

(73) Assignee: Nanobubbling, LLC, Austin, TX (US)

( * ) Notice: Subject to any disclaimer, the term of this patent is extended or adjusted under 35 U.S.C. 154(b) by 0 days.

(21) Appl. No.: 16/115,066

(22) Filed: Aug. 28, 2018

(65) Prior Publication Data

US 2019/0060223 A1 Feb. 28, 2019

Related U.S. Application Data

(63) Continuation-in-part of application No. 15/850,362, filed on Dec. 21, 2017.
(Continued)

(51) Int. Cl.
| | | |
|---|---|---|
| *B01F 3/04* | (2006.01) | |
| *B01F 5/04* | (2006.01) | |
| *A61K 9/00* | (2006.01) | |
| *A61K 9/08* | (2006.01) | |
| *A61K 33/00* | (2006.01) | |

(52) U.S. Cl.
CPC .......... *A61K 9/0019* (2013.01); *A61K 9/0014* (2013.01); *A61K 9/08* (2013.01); *A61K 33/00* (2013.01); *B01F 3/04248* (2013.01); *B01F 3/04503* (2013.01); *B01F 5/0465* (2013.01);
(Continued)

(58) Field of Classification Search
CPC .... B01F 2003/0439; B01F 2003/04858; B01F 3/04262; B01F 5/0465
See application file for complete search history.

(56) References Cited

U.S. PATENT DOCUMENTS

| | | |
|---|---|---|
| 8,481,077 B2 | 7/2013 | Kheir |
| 8,919,747 B2 | 12/2014 | Anzai et al. |
| (Continued) | | |

FOREIGN PATENT DOCUMENTS

| | | |
|---|---|---|
| WO | 2009043031 A2 | 4/2009 |
| WO | 2017172887 A1 | 10/2017 |

OTHER PUBLICATIONS

Bisazza et al., "Microbubble-Mediated Oxygen Delivery to Hypoxic Tissues as a New Therapeutic Device," 30th Annual International IEEE EMBS Conference, Vancouver, BC, pp. 2067-2070, Aug. 20-24, 2008.
(Continued)

*Primary Examiner* — Michael B. Pallay
(74) *Attorney, Agent, or Firm* — Matheson Keys & Kordzik PLLC; Kelly Kordzik

(57) ABSTRACT

A nanobubbler includes a porous ceramic material, a first inlet configured to inject a gas into the porous ceramic material, wherein the porous ceramic material is configured to emit nanobubbles into the chamber from the surface in response to the injection of the gas, a chamber positioned adjacent to a surface of the porous ceramic material, a second inlet configured to inject a liquid into the chamber so that the nanobubbles are dislodged from the surface of the porous ceramic material into the liquid, and an outlet configured to output from the chamber the liquid infused with the nanobubbles. The nanobubbles infused into the liquid have an average diameter of less than 500 nanometers.

18 Claims, 7 Drawing Sheets

Related U.S. Application Data

(60) Provisional application No. 62/551,356, filed on Aug. 29, 2017.

(52) U.S. Cl.
CPC ............... *B01F 2003/04858* (2013.01); *B01F 2003/04879* (2013.01); *B01F 2003/04893* (2013.01)

(56) References Cited

U.S. PATENT DOCUMENTS

| | | | | |
|---|---|---|---|---|
| 2006/0284325 | A1* | 12/2006 | Kohama | B01F 3/04262 261/122.1 |
| 2014/0191425 | A1* | 7/2014 | Yano | B01F 3/04262 261/124 |
| 2017/0259219 | A1* | 9/2017 | Russell | C02F 1/685 |

OTHER PUBLICATIONS

Cavalli et al., "Preparation and characterization of dextran nanobubbles for oxygen delivery," International Journal of Pharmaceutics, vol. 381, pp. 160-165, Jul. 17, 2009.

Roe et al, "Topical Dissolved Oxygen Penetrates Skin: Model and Method," Journal of Surgical Research, vol. 159, pp. e29-e36, May 28, 2009.

Aliabouzar, M. et al., "Lipid Coated Microbubbles and Low Intensity Pulsed Ultrasound Enhance Chondrogenesis of Human Mesenchymal Stem Cells in 3D Printed Scaffolds," Sci. Rep. 6, 37728; doi: 10.1038/srep377728 (2016).

Chaplin, M., "Nanobubbles (Ultrafine bubbles)," www.lsbu.ac.ukwater/nanobubble.html, 2007.

Ebina, K. et al., "Oxygen and Air Nanobubble Water Solution Promote the Growth of Plants, Fishes, and Mice," Published: Jun. 5, 2013https://doi.org/10.1371/journal.pone.0065339.

Liu, S. et al., "Nano-bubbles' effects on the physicochemical properties of water—the basis of peculiar properties of water containing nano-bubbles," International Conference on Agricultural Engineering, Synergy in the Technical Development of Agriculture and Food Industry GÖDÖLLÖ, 2011.

Liu, S. et al., "Effects of nanobubbles on the physicochemical properties of water: The basis for peculiar properties of water containing nanobubbles," Chemical Engineering Science, vol. 93, Apr. 19, 2013, pp. 250-256.

Liu, S. et al., "Oxidative capacity of nanobubbles and its effect on seed germination," ACS Sustainable Chem. Eng. 2016.

Matsuki, N. et al., "Oxygen supersaturated fluid using fine micro/nanobubbles," International Journal of Nanomedicine, vol. 9, Issue 1, Sep. 23, 2014.

Morrow, D.I.J. et al., "Innovative Strategies for Enhancing Topical and Transdermal Drug Delivery," The Open Drug Delivery Journal, 2007.

Nishimura, N. et al., "Effects of repeated carbon dioxide-rich water bathing on core temperature, cutaneous blood flow and thermal sensation," Eur J Appl Physiol (2002) 87: 337-342.

Scheuplein, R., "Permeability of the Skin: A Review of Major Concepts and Some New Developments," The Journal of Investigative Dermatology, 61:672-676. 1976.

"Diabetic Foot Ulcer Treatment Using Hyperbaric Oxygen Therapy Guide," Sechrist Industries, Inc., 2008.

\* cited by examiner

FIG 7

| | I. Shearing Force Method | II. Precipitation of Dissolved Gas as Bubbles | III. Mixing Saturated Steam into Liquid | IV. Nanobubbler 100 |
|---|---|---|---|---|
| Bubble size | microbubbles | microbubbles | microbubbles | nanobubbles |
| Ease to scale up | ▲ no | no | ◎ yes | ○ yes |
| Gas transfer efficiency | ~60% | ~65% | ~65% | ~95% |
| Use of high viscosity liquid | ▲ no | △ no | no | ◎ yes |
| Use of liquid containing foreign material | no | yes | yes | yes |
| Use of high temperature liquid | yes | no | yes | yes |
| System concatenation | no | no | △ no | ◎ yes |
| Self air-absorption | yes | no | no | no |
| System integration | △ no | △ no | △ no | yes |
| Suitable for a variety of applications | ○ yes | yes | △ no | ◎ yes |
| Miniaturization | no | no | no | ◎ yes |
| Cost effective | no | yes | no | ○ yes |

Key:
▲ Very difficult
△ Problematic
○ Better
◎ Superior

# NANOBUBBLER

This application claims priority to U.S. provisional application No. 62/551,356, and is a continuation-in-part of U.S. patent application Ser. No. 15/850,362, both of which are hereby incorporated by reference herein. This application is related to U.S. provisional application No. 62/490,800 and U.S. provisional application No. 62/437,920, both of which are hereby incorporated by reference herein

TECHNICAL FIELD

The present disclosure relates in general to a production of nanobubbles, and in particular, to an apparatus for producing nanobubbles in a liquid.

BACKGROUND INFORMATION

This section is intended to introduce various aspects of the art, which may be associated with exemplary embodiments of the present disclosure. This discussion is believed to assist in providing a framework to facilitate a better understanding of particular aspects of the present disclosure. Accordingly, it should be understood that this section should be read in this light, and not necessarily as admissions of prior art.

There are many applications related to transdermal and topical drug delivery (e.g., see, D. I. J. Morrow et al., "Innovative Strategies for Enhancing Topical and Transdermal Drug Delivery," The Open Drug Delivery Journal, 2007, vol. 1, pp. 36-59). A good example is the external oxygen supply in the hyperbaric process (e.g., see "Diabetic Foot Ulcer Treatment Using Hyperbaric Oxygen Therapy Guide," published by Sechrist Industries, Inc., copyright 2008). Human skin acts as a protective barrier, which keeps noxious substances out of the body and inhibits excessive loss of water from the internal organs. Nevertheless, strategies have been developed to deliver drugs to the skin and surpass the skin's barrier properties.

For example, it is known that carbon dioxide, when it is able to penetrate through the skin, has a positive effect of expanding blood vessels and thus naturally improving blood flow (known as The Bohr Effect). This effect has been observed numerous times when bathing in carbonated springs with high concentrations of carbon dioxide (e.g., see N. Nishimura et al., "Effects of repeated carbon dioxide-rich water bathing on core temperature, cutaneous blood flow and thermal sensation," Eur. J. Appl. Physiol., vol. 87, pp. 337-342, Jun. 7, 2002).

It has been demonstrated that a cutaneous uptake of atmospheric oxygen contributes significantly to oxygen supply to the human dermis and epidermis. Oxygen can be supplied in such a manner to the upper skin layers at depths of 0.25 mm to 0.4 mm.

Based on the example above, one can come to a conclusion that a cutaneous external application of gasses (such as oxygen, carbon dioxide, ozone, etc.) can have very positive effects on the health of human beings in the same way as transdermal drug delivery. An important factor in such a drug delivery method is the permeability through the skin (e.g., see R. J. Scheuplein, "Permeability of the Skin: A Review of Major Concepts and Some New Developments," The Journal of Investigative Dermatology, vol. 67, no. 5, pp. 672-676, 1976).

If one wants to use a cutaneous external application of gasses, one needs to find ways to provide penetration enhancers for the specific gasses utilized such that an optimal transdermal delivery can be achieved.

Gas nanobubbles for which the radius is less than 500 nm, have peculiar properties that if supplied cutaneously and externally to the human skin have a high probability of permeability through the skin, which may be further enhanced by physical and chemical enhancers that are applied in transdermal drug delivery (e.g., see, T. Higuchi, "Physical Chemical Analysis of Percutaneous Absorption Process from Creams and Ointments," Journal of the Society of Cosmetic Chemists, pp. 85-97, 1959).

Nanobubbles are defined as gas-filled cavities in a solution (e.g., a water solution) with each of the nanobubbles having a diameter of less than 500 nm. Nanobubbles possess some peculiar properties such as minimal to no buoyancy effects, the nanobubble gas/liquid interface is negatively charged, due to their charge nanobubbles repel each other, nanobubbles avoid coalescence and dissipation, nanobubbles are stable in liquid (e.g, for at least several days), gas nanobubbles in a liquid contribute increased concentration of the dissolved gas in the liquid, gas nanobubbles (when properly generated) exhibit a very high density within the liquid carrier (e.g., $10^8$-$10^9$ bubbles/mL), and due to their nano-diameter the nanobubbles have a very large interfacial area.

Based on a publication by Martin Chaplin (see, http://www1.lsbu.ac.uk/water/martin_chaplin.html), the approximate ranges of bubble generation are as presented in FIG. 4, which illustrates the density of microbubbles and nanobubbles in liquid as a function of their generated size. As one can observe, microbubbles are defined in the range of 10 μm to 100 μm in diameter (with a central density of approximately $10^4$ to $10^6$ bubbles/mL), while nanobubbles are defined in the range of less than 1 μm, and primarily less than 500 nm (with a density of approximately between $10^8$ and $10^9$ nanobubbles/mL).

Using simple calculations as well as what is demonstrated in FIG. 4, if one generates bubbles that are smaller in diameter than 500 nm the concentration of the nanobubbles should be on the order of $10^8$ to $10^9$ nanobubbles/mL. On the other hand, if the bubbles concentration is on the order of $10^4$ to $10^6$ bubbles/mL, the expected diameter of the bubbles is approximately 10 μm, which are microbubbles by definition. Basically, if one claims that his generator creates nanobubbles, then the measured concentration in a liquid should be around $10^8$ nanobubbles or higher.

BRIEF DESCRIPTION OF THE DRAWINGS

FIG. 7 illustrates a comparison between different methods of creating bubbles in a liquid.

DETAILED DESCRIPTION

Embodiments of the present disclosure utilize porous ceramics, and the simplest and cheapest way is to use commercially available porous ceramics without modifying their proprietary processes for producing these. Unfortunately, these ceramics when molded in different shapes can only achieve pores with a narrow distribution of larger than 1 µm and in general, the pores have a distribution that can go up to 50 µm. In order to obtain smaller pores, typical devices have been carbon-based (e.g., see U.S. Pat. No. 8,919,747), but are only able to create "super-micro bubbles of several hundred nanometers to several dozen microns in diameter. Obviously, if one wants to create effective nanobubbles (i.e., smaller than or equal to 500 nm), it will be difficult to obtain a narrow distribution around the smallest pore diameter that can presently be achieved with such commercially available devices.

Applicants have developed a nanobubbler that has been proven to create nanobubbles of gasses such as oxygen, carbon dioxide, nitrogen, NO, etc., in the desired concentrations and sizes. Embodiments of the present disclosure utilize a porous ceramic (which may be made without any added carbon or graphite material) as the medium (i.e., diffuser) for creating gas nanobubbles. As will be further disclosed, certain embodiments of the present disclosure are able to properly adjust the sizes of the pores vis-à-vis the surface energy of the diffuser material such that a strong stream of liquid on the face of the diffuser will be able to dislodge the gas bubbles with ease.

Figure 1:
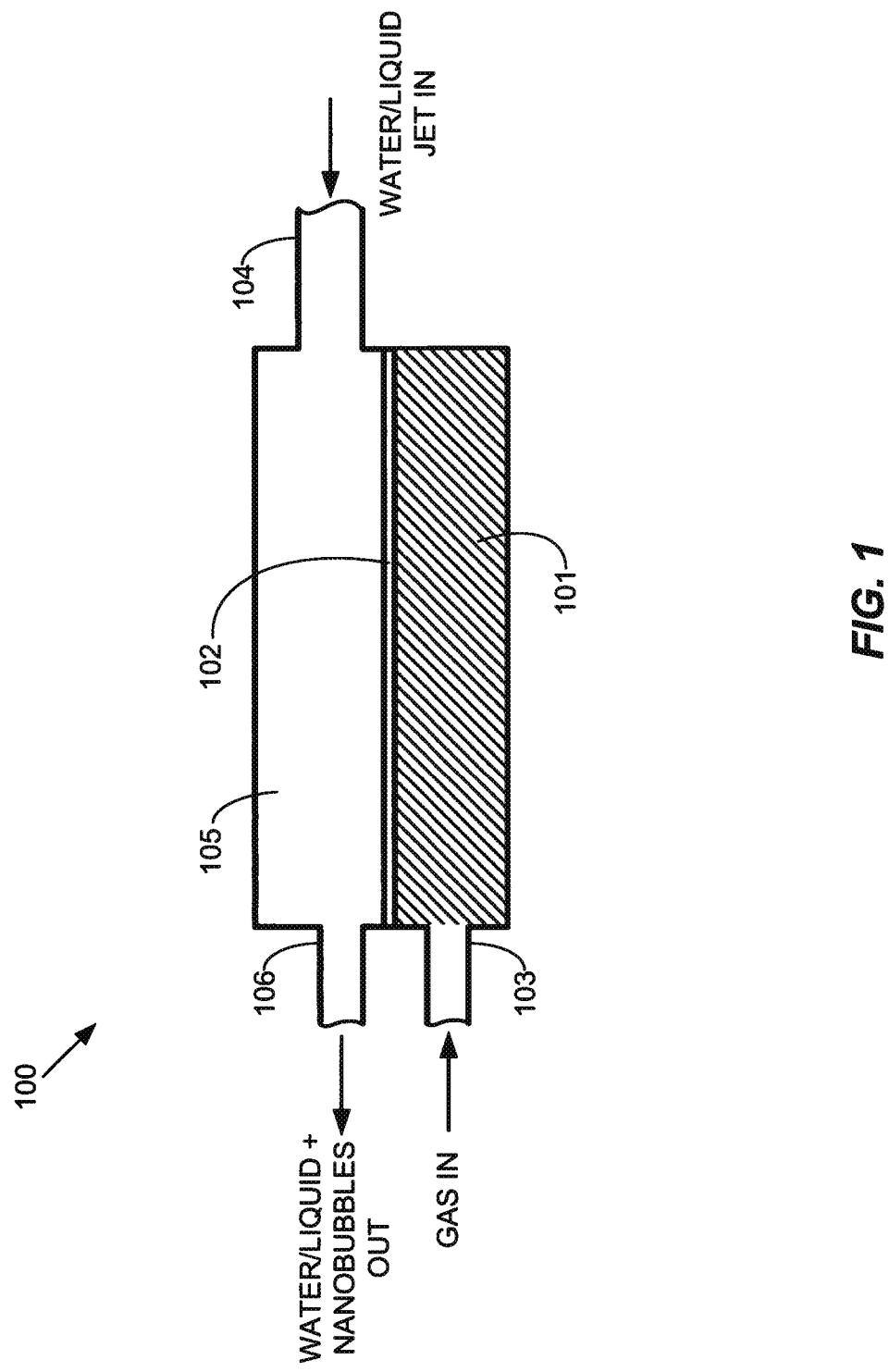
FIG. 1 illustrates a cross-section of a nanobubbler configured in accordance with embodiments of the present disclosure.

As illustrated in FIG. 1, embodiments of the present disclosure implement a nanobubbler 100 configured to have the nanobubbles emit only from one or more selected surfaces 102 such that the cross-sectional area of the liquid flow can be controlled, and as a result its pressure and flow intensity.

As shown in the illustrated cross-section of the nanobubbler 100 of FIG. 1, the gas is injected under a predetermined pressure, via the inlet 103, into the diffuser 101, while the liquid (e.g., water) is injected, via the inlet 104, into the adjoining chamber 105 so that it passes across the surface 102 of the diffuser, which is emitting the nanobubbles into the liquid through the naturally formed pores. The nanobubble-infused liquid then exits via the outlet 106.

The nanobubbler 100 may be made of a high-density porous ceramic material (e.g., aluminum oxide) with pores less than 1 µm, including many about 0.5 µm and less. In accordance with embodiments of the present disclosure, the porous ceramic material may have no added carbon. In accordance with embodiments of the present disclosure, the nanobubbler 100 may have a substantially rectangular shape whereby the liquid flow through the chamber 105 is laminar and parallel to the surface of the diffuser that is emitting the nanobubbles. Therefore, the nanobubbler 100 can be made at a lower cost than typical bubblers on the market, and as a result will considerably augment the number of applications. In accordance with embodiments of the present disclosure, the nanobubbler 100 may have an internal cavity into which the gas is injected.

Figure 5:
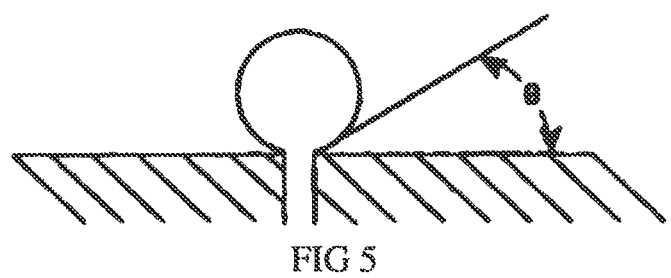
FIG. 5 schematically illustrates surface energy and a desired shape of a gas nanobubble on the surface of a diffuser.

It is understood that while the pore sizes in the diffuser 101 play an important function in creating nanobubbles of a desired diameter, other important factors are the ratio of the surface energy of the diffuser material at the water interface to the surface energy of the liquid, and the ratio of the surface energy of the diffuser material to the gas surface energy. Embodiments of the present disclosure are configured to promote a "beading" of the gas nanobubbles on the surface of the diffuser. As illustrated in FIG. 5, such a beading of the gas nanobubbles as they are generated on the surface of the diffuser from the pores results in a desired contact angle between the gas nanobubbles and the surface of $0°<\Theta\leq90°$ in order that a stream of liquid (e.g., water) propelled through the chamber 105 and parallel to the diffuser surface will efficiently dislodge the gas nanobubbles from the surface of the diffuser.

To accomplish this, in accordance with embodiments of the present invention, the surface of the diffuser 101 may be physically treated (e.g., polished using any well-known techniques) so that such a surface is very smooth and thus applies a decreased frictional force upon the passing liquid in the chamber 105. In accordance with embodiments of the present invention, the surface of the diffuser may be modified (e.g., physically treated, such as polished) so that the ratio of the surface energy of the liquid to the surface energy of the surface of the diffuser promotes a contact angle of the generated nanobubbles of $0°<\Theta\leq90°$. Additionally, in accordance with embodiments of the present invention, the surface of the diffuser may be modified (e.g., physically treated, such as polished) so that the ratio of the surface energy of the nanobubbles to the surface energy of the surface of the diffuser promotes a contact angle of the generated nanobubbles of $0°<\Theta\leq90°$.

Furthermore, the flow rate of the liquid through the chamber 105 may be adjusted so that it is capable of removing the generated nanobubbles before their diameters grow larger than a desired dimension (e.g., an average diameter within any desired range <500 nm in certain embodiments, or an average diameter within any desired range <200 nm in certain embodiments, or an average diameter within any desired range <100 nm in certain embodiments).

Another problem in the utilization of existing commercially available diffusers is that the pores are larger than desired and have a large distribution of sizes that is ineffective for producing a high density of nanobubbles. In accordance with embodiments of the present invention, high quality ceramics are commercially acquired from vendors, and then using processes described herein, the sizes of the emitting pores can be customized. In such a case, one can obtain between 100 nm to 600 nm pores that are satisfactory for creating nanobubbles (diameters less than 500 nm) and minibubbles (diameters greater than 500 nm and less than or equal to 1 µm).

In accordance with certain embodiments of the present invention, the nanobubbler 100 may be configured with a film 102 deposited over the top of the emitting surface(s) that provides an external control of the diameters of the emitting pores achieving both narrower pores and a much narrower distribution of the resultant pore diameters.

Figure 2:
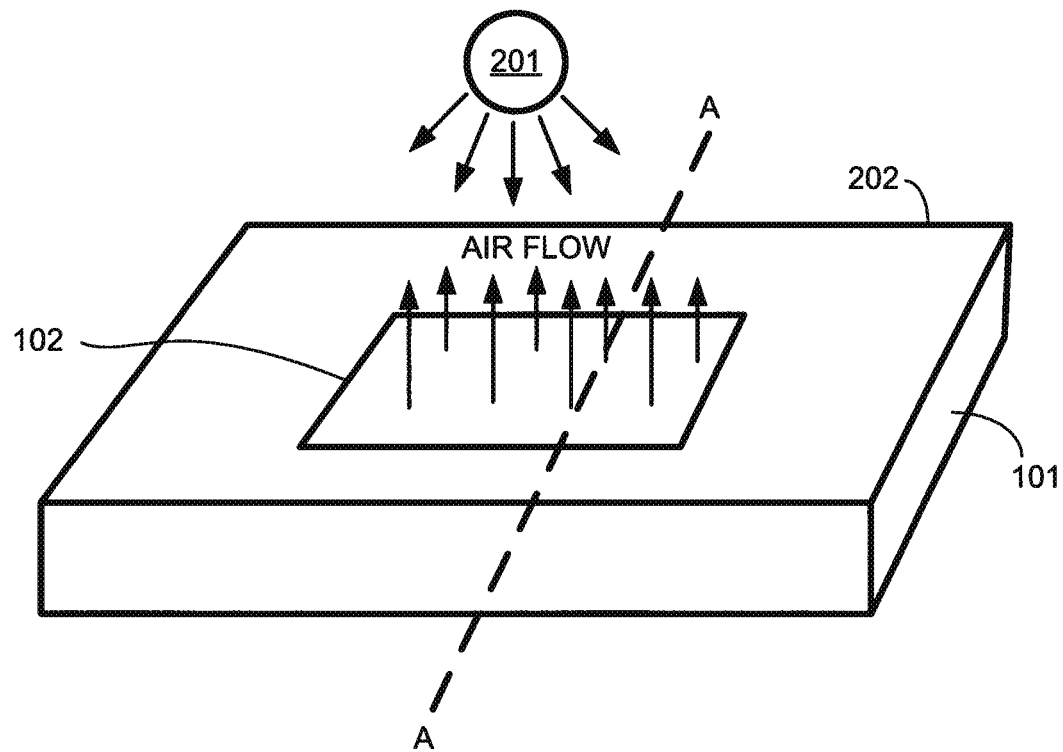
FIG. 2 illustrates an isometric view of a portion of a nanobubbler configured in accordance with embodiments of the present disclosure.
Figure 3A:
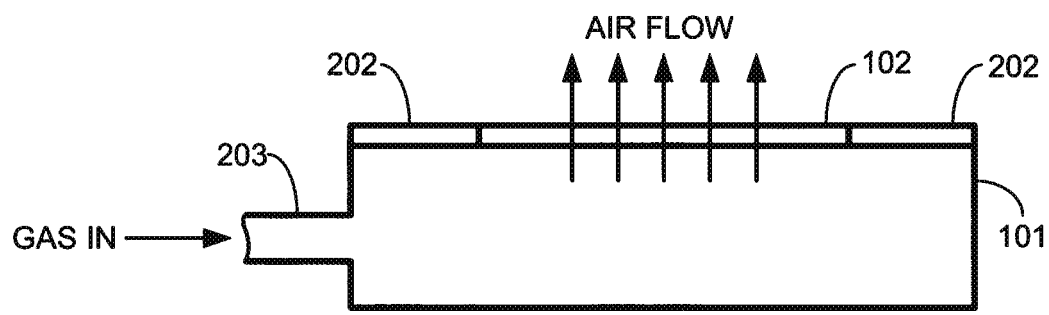
FIG. 3A illustrates a cross-section of the diffuser of the nanobubbler of FIG. 2 taken along the line A-A'.
Figure 3B:
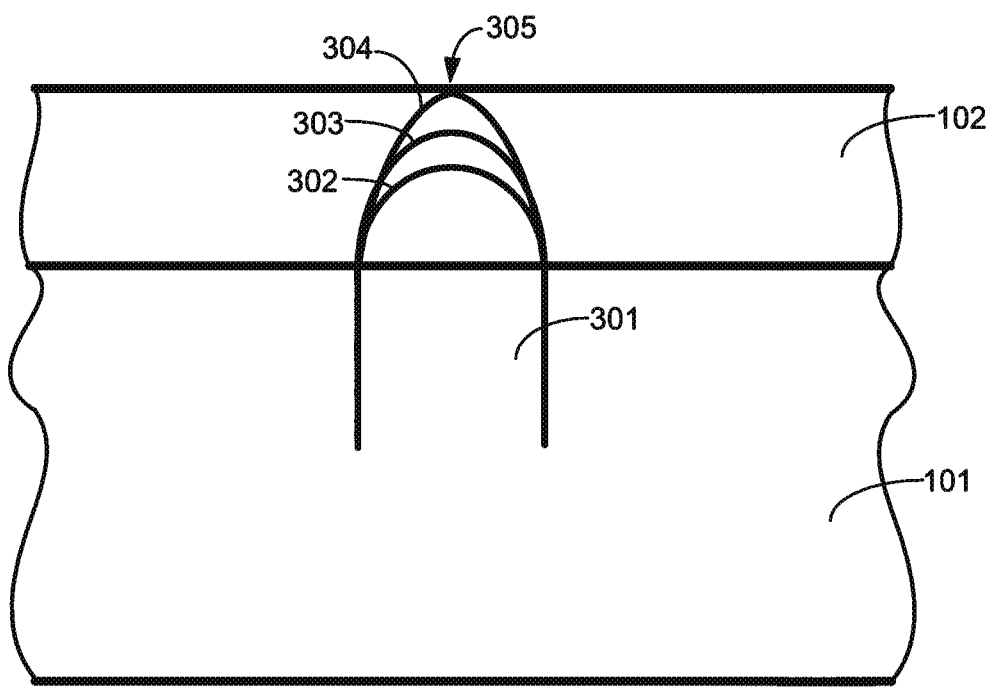
FIG. 3B illustrates a magnified portion of the diffuser showing a generation of a pore within the nanobubbler of FIG. 3A in accordance with embodiments of the present disclosure.
Figure 4:
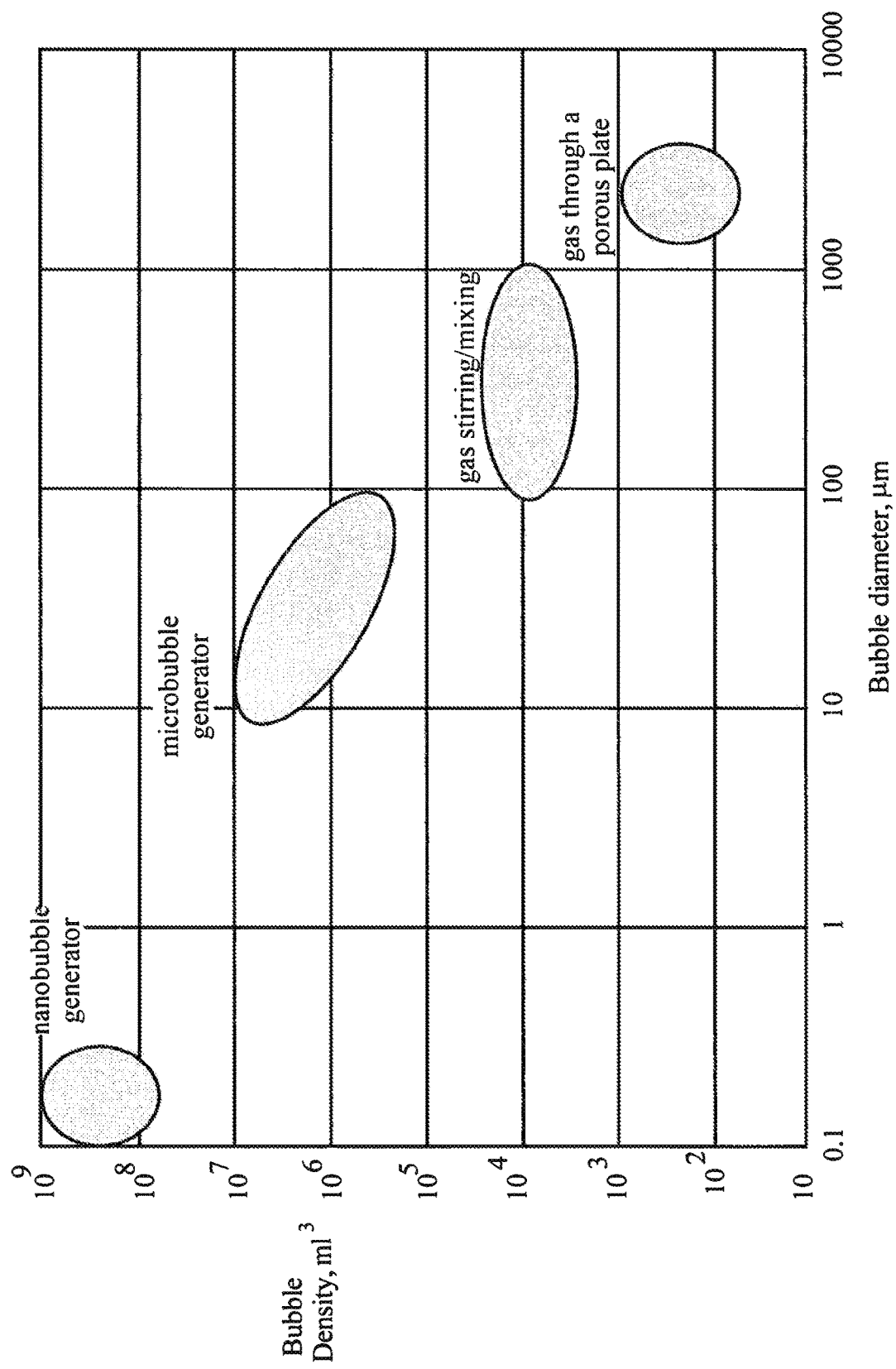
FIG. 4 illustrates the density of microbubbles and nanobubbles in liquid as a function of their generated size.

Referring to FIGS. 2-3B, an exemplary film 102 that can be utilized is a UV curable epoxy (or similar UV curable polymeric materials). FIG. 3A illustrates a cross-section of the diffuser 101 illustrated in FIG. 2 taken along the dashed line A-A'. In this case, the emitting surface 202 of the diffuser 101 is covered (wholly or partially) by a liquid UV curable epoxy film 102 such that before the irradiation of UV light from a UV light source 201, air (or any gas for this purpose) is continuously flowing (e.g., via an inlet 203) through the pores of the diffuser 101 under high pressure such that the diameters of the respective pores created in the film 102 can be controlled (via the applied gas pressure), and then the resultant pore structure created in the film 102 can be fixed by the UV curing process, which may be performed in parallel with the gas flow.

Referring to FIG. 3B, there is illustrated a magnified portion of FIG. 3A showing how this process may be performed. After the liquid UV curable epoxy is deposited on the surface of the diffuser 101, a pressurized gas supply is coupled to the inlet 203 to the diffuser 101. As the gas is injected into the diffuser 101, it will be forced into each pore 301, and will attempt to exit the diffuser 101 through the liquid UV curable epoxy film 102. It can be readily appreciated that over a time period, the gas exiting the diffuser pore 301 pushes through the film 102 as illustrated in FIG. 3B by the depicted time-lapsed penetrations 302, 303, 304, which show successive penetrations of the gas through the film 102. Eventually, the gas will break through the film 102 forming a pore opening 305 on the surface of the film 102 of a size that is smaller than the size of the pore 301 of the diffuser 101. The UV light 201 is then applied to the film 102 to affix the achieved size of the newly formed pore opening 305.

In such a way, one can achieve a decreasing of the diameters of the resultant emitting pores and also control the distribution (range) of pore diameters in an emitting surface of the film 102.

Other similar materials polymeric in nature may alternatively be utilized with UV curing (or any other curing method that can achieve the desired solution as explained above).

In accordance with certain embodiments of the present invention, the surface of the cured epoxy film 102 may be physically treated (e.g., polished) in order to result in a more significant "beading" of the gas nanobubbles as they are generated, similar to the previous discussion with respect to the physical treatment of the surface of the diffuser 101.

Furthermore, if one wants to have emission of nanobubbles from one surface only, then one must have means to plug the pores on the undesirable surfaces. In such a way, one can direct the nanobubble emission to one or more surfaces as desired. Embodiments of the present disclosures achieve that by using a suitable epoxy material that is cured on the un-utilized surfaces 202, such as illustrated in FIGS. 2 and 3A.

By eliminating the requirement for using all the surfaces available for creating bubbles in embodiments of the present invention, it is relatively easy to have the inlets of the gas and of the fluid on the same lateral wall eliminating in such a way the complexity of the nanobubbler configuration, and simplifying the integration of the nanobubbler 100 with any necessary external parts.

As a result, the nanobubbler 100 may be configured to produce a combination of microbubbles and nanobubbles with a larger proportion of nanobubbles with respect to the microbubbles, wherein the nanobubbles have a size distribution of less than 500 nm in certain embodiments, or even less than 200 nm in certain embodiments, or even less than 100 nm in certain embodiments.

Figure 6:
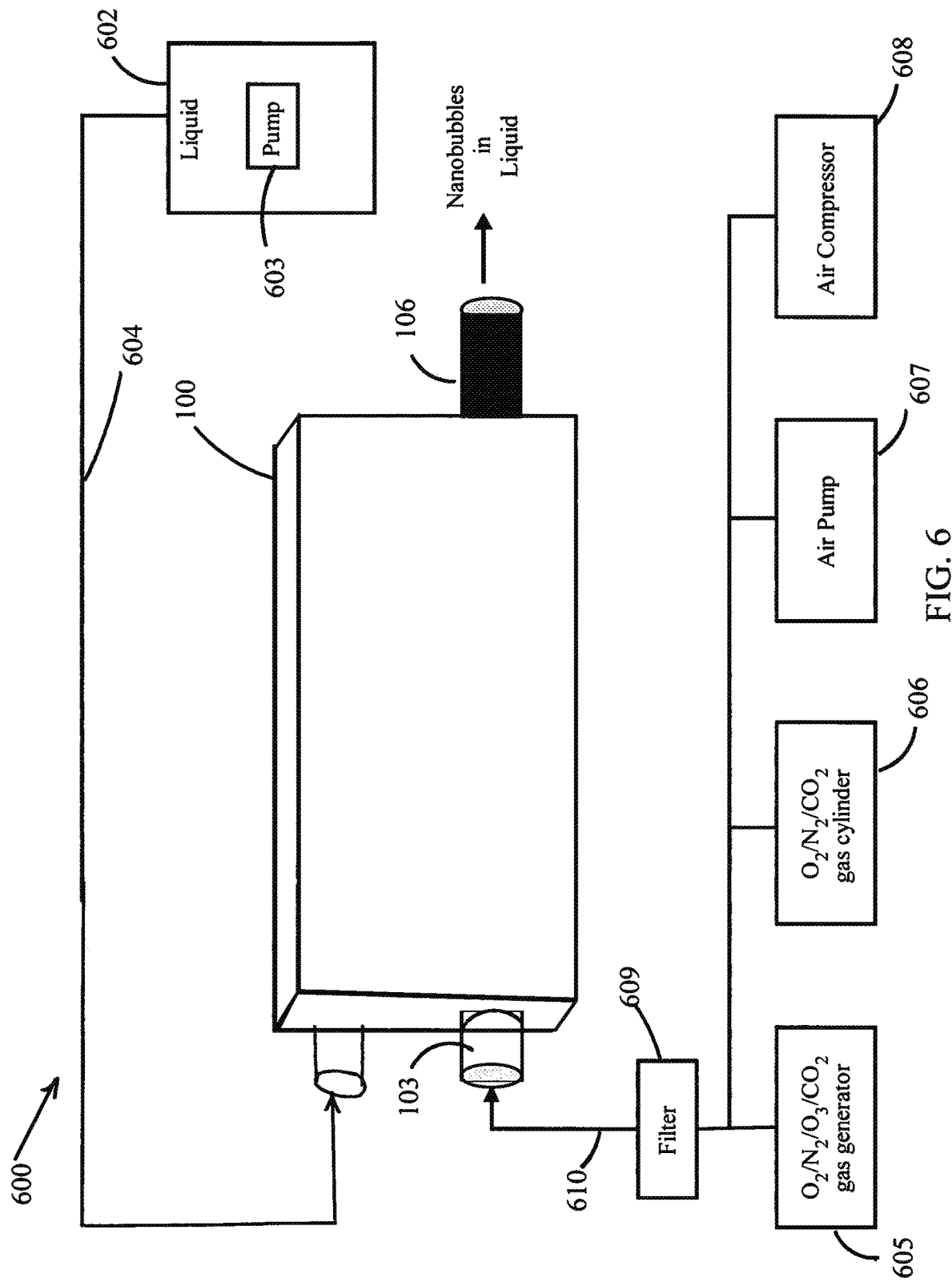
FIG. 6 illustrates a block diagram of a nanobubble generator configured to generate nanobubbles and infuse them into a liquid using a nanobubbler.

FIG. 6 illustrates a block diagram of an apparatus 600 (also referred to herein as a nanobubble generator) configured to generate nanobubbles and infuse them into a liquid using the nanobubbler 100. The generated nanobubbles may contain any one or more desired gasses (e.g., oxygen ($O_2$), nitrogen ($N_2$), $CO_2$, $O_3$, air, and/or any other desired gas), which may be received from a source, such as from one or more of a gas generator 605 configured to supply such gas(es), one or more pressurized gas cylinders 606 (or from a cylinder that contains a compatible combination of such desired gasses), an air pump 607, and/or an air compressor 608. The supplied gas may be filtered by a filter 609 before being supplied to the nanobubbler 100 at a first inlet 103. An appropriate liquid may be contained within a receptacle 602, and a pump 603 utilized to pump the liquid over the supply line 604 to a second inlet 104. The nanobubbles are generated and infused into the liquid. The liquid with the infused nanobubbles then exits from the outlet 106, where it can then be utilized for the various applications described herein (e.g., medical, therapeutic, cosmetic, etc.).

Note that the apparatus 600 may include a plurality of nanobubblers 100, each configured to generate nanobubbles in the liquid containing a different type of gas (e.g., oxygen ($O_2$), nitrogen ($N_2$), $CO_2$, $O_3$, air, and/or any other desired gas). The liquid may be pumped through a combination of such plurality of nanobubblers 100, and then the liquid combined as it exits from each nanobubbler 401 for resulting contact with a person's skin. Alternatively, a single nanobubbler 100 may be configured to generate nanobubbles in the liquid with a plurality of different gasses (e.g., oxygen ($O_2$), nitrogen ($N_2$), $CO_2$, $O_3$, air, and/or any other desired gas), whereby either the different plurality of gasses are simultaneously passed through the diffuser 101, or in an intermittent basis, one after the other.

Exemplary Non-Limiting Nanobubbler Apparatus Specifications:

Dimensions of the diffuser 101: 160×35×22 (mm)
Pore dimensions of the diffuser 101: <1 micron
Pressure of injected gas: 5-10 psi
Liquid flow through the chamber 105: 5-15 liters/minute
Water Nozzle: ϕ15 mm
Gas Nozzle: ϕ6 mm
Body case material: PVC
Nanobubbler envelope dimensions: 220×50×50 (mm)

Note that such specifications for a nanobubbler may be dependent upon the particular gas, or gases, to be contained within the generated nanobubbles, and also dependent upon the viscosity of the liquid within which the nanobubbles are infused.

Furthermore, the apparatus 600 may be utilized to form the pores in the UV curable epoxy film as previously described with respect to FIGS. 2-3B.

In order to properly characterize the production of nanobubbles the inventors investigated and identified the proper equipment to do so. The inventors discovered at least three companies that their equipment can be utilized to measure nanobubbles of gas in water: Horiba, Izon Science Ltd., and Malvern Panalytical Ltd.

The results were very similar for equivalent samples sent to all three companies. A sample of water containing carbon dioxide nanobubbles generated with the nanobubbler 100 was measured utilizing a NanoSight NS300 instrument commercially available from Malvern Panalytical Ltd.

The measurements revealed that a majority of the generated nanobubbles were smaller than 200 nm. Furthermore, the concentration of the nanobubbles within the liquid was approximately $10^8$ nanobubbles/mL as expected. Additionally, the nanobubbles remained very stable in the water for at least 3 months.

A comparison between different methods of creating bubbles in a liquid, including using the nanobubbler 100 is presented in FIG. 7. Generally, the methods I, II, and III will produce microbubbles having a diameter greater than 10 microns, while the nanobubbler is capable of producing nanobubbles with a diameter less than 1 micron, and particularly less than 500 nm. The ease to scale up factor pertains to a capability to scale up the size of the apparatus in order to scale up the manufacturing volume. Gas transfer efficiency refers to a percentage of the injected gas that is eventually emitted as bubbles into the liquid. A liquid containing a foreign material refers to the capability of containing some other compound either within the gas nanobubbles or within the liquid. System concatenation refers to a capability to daisy-chain several bubblers in a chain for infusing different gases into the liquid. Self air-absorption refers to the apparatus being resistant to absorbing ambient air into the system, which can contaminate the infused nanobubbles and liquid. System integration refers to a capability to incorporate the apparatus into another manufacturing or application device.

The potential applications of nanobubbles generated by the nanobubbler 100 are various:

Enhanced ultrasound imaging due to increased reflection of the sound waves (MEDICAL).
Enhanced tumor ultrasound imaging (MEDICAL).
Extraction of oil in an oil recovery process by in situ downhole $CO_2$ flooding (OIL INDUSTRY).
Nucleation of crystals (SCIENCE).
Surge dissipation in pump-like systems having long liquid pipelines (OIL INDUSTRY).
Algal biofuel production (AGRICULTURE).
Waste water aeration (WASTEWATER REMEDIATION).
Ozone dosing for strong oxidation and disinfection (FOOD INDUSTRY).
Flotation separation (suspended matter, colloids, emulsions, etc.) (OIL & WASTEWATER INDUSTRIES).
Gas-liquid scrubber in common chemical reactions (ENVIRONMENT CLEANING).
Oxidization of oxygen depleted water (ENVIRONMENT CLEANING).
Rapid humidification in salinization plants (WATER INDUSTRY).
Improved heat transfer and vaporization promotion (ENERGY)
Biomedical applications, such as protein separation and cells activation (MEDICAL).
Degradation of viscosity (COSMETICS AND PHARMACUETICALS).
Improvement of shrimp/fishery industries (FOOD INDUSTRY).
Soil preservation and aeration (AGRICULTURE).

With respect to agriculture, the nanobubbler 100 can produce nanobubbles, in particular oxygen nanobubbles (or even air), which is of a very high importance. There are three principles where nanobubbles can revolutionize agriculture by enhancing water oxygenation, higher speed of nutrient solubility, and reduction of viscosity.

Water oxygenation is very important for avoiding root suffocation (hypoxia and anoxia) as a result of lack of oxygen in the soil. As an example, if you have too much rain, the stagnant water in the soil occupies the spaces previously filled with air, and the oxygen in the air remains present only in the first few layers of the soil. Obviously this creates root suffocation.

Higher speed of nutrient solubility: The plant absorption rate of a nutrient depends on its rate of dissolution in water and the rate of diffusion into the root. The speed of dissolution can be increased by "shaking" and by increasing the contact surface. The nanobubbles, due to their stability and longevity in water, will do exactly that: they increase the specific area between water and nutrients by continuous motion and bombardment that is similar to "shaking."

Reduction of viscosity: A water molecule is an electric dipole. Due to this property, water molecules stand to create hydrogen bonds that is a legitimate bond but weaker than the covalent bond. But these hydrogen bonds basically define the physical characteristics of water including viscosity and surface tension. The hydrogen bonds allow more molecules to join together via dipole-dipole interactions, and as a result, the water molecules form clusters of molecules lowering in such a way the viscosity, allowing the roots to absorb water more easily.

The following publications describe these in more detail:
I. https://www.cabdirect.org/cabdirect/abstract/20093272389
II. http://aura-tec.com/pdf/Chemical_Engineering_Science%2093.pdf
III. http://www.hae-journals.org/archives/haen_23/HAE_23_18.pdf
IV. https://s3-eu-west-1.amazonaws.com/pstorage-acs-6854636/3733321/sc5b01368_si_001.pdf
V. http://journals.plos.org/plosone/article?id=10.1371/journal.pone.0065339
VI. https://www.ncbi.nlm.nih.gov/pubmed/11541572

In general, the use of nanobubble technology on plant growth was discussed in 2015 with no reference to nanobubbles that basically will have an exponentially higher effect than the use of larger bubbles. See for example, http://www.internationaljournalssrg.org/IJCE/2015/Special-Issue/NCRACCESS-2015/Part-2/IJCE-NCRACCESS-P108.pdf.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

It will be understood that particular embodiments described herein are shown by way of illustration and not as limitations of the invention. The principal features of this invention can be employed in various embodiments without departing from the scope of the invention.

All publications and patent applications are herein incorporated by reference to the same extent as if each individual publication or patent application was specifically and individually indicated to be incorporated by reference.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a" and "an" mean "one or more" when used in this application, including the claims.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

What is claimed is:

1. A nanobubbler comprising:
   a porous ceramic material, wherein the porous ceramic material does not include any carbon;
   a chamber positioned adjacent to a surface of the porous ceramic material;
   a first inlet configured to inject a gas into the porous ceramic material, wherein the porous ceramic material is configured to emit nanobubbles into the chamber from the surface in response to the injection of the gas;
   a second inlet configured to inject a liquid into the chamber so that the nanobubbles are dislodged from the surface of the porous ceramic material into the liquid; and
   an outlet configured to output from the chamber the liquid infused with the nanobubbles.

2. The nanobubbler as recited in claim 1, wherein the nanobubbles have an average diameter of less than 500 nanometers.

3. The nanobubbler as recited in claim 1, wherein the nanobubbles have an average diameter of less than 200 nanometers.

4. The nanobubbler as recited in claim 1, wherein the nanobubbles have an average diameter of less than 100 nanometers.

5. The nanobubbler as recited in claim 1, wherein the surface of the porous ceramic material is substantially planar.

6. The nanobubbler as recited in claim 1, wherein the surface of the porous ceramic material is configured so that the emitted nanobubbles have a contact angle of 0°-90°.

7. The nanobubbler as recited in claim 1, wherein the liquid is selected from the group consisting of water, alcohol, oil, and any combination thereof.

8. The nanobubbler as recited in claim 1, wherein the liquid output from the chamber is infused with the nanobubbles in a concentration of approximately $10^8$ nanobubbles/mL or greater.

9. The nanobubbler as recited in claim 1, wherein the liquid is injected into the chamber at 5 liters per minute or greater.

10. The nanobubbler as recited in claim 9, wherein the nanobubbles are emitted from pores in the porous ceramic material, wherein the pores have a diameter in a range of less than one micron, and wherein the gas is injected into the porous ceramic material at a pressure of 5 psi or greater.

11. The nanobubbler as recited in claim 9, wherein the liquid is injected into the chamber parallel to the surface of the porous ceramic material.

12. The nanobubbler as recited in claim 1, wherein the porous ceramic material is in a rectangular form having six sides that is configured so that the nanobubbles are emitted only from a first side of the six sides of the porous ceramic material.

13. The nanobubbler as recited in claim 1, wherein the surface of the porous ceramic material has been modified so that a ratio of a surface energy of the nanobubbles to a surface energy of the surface of the porous ceramic material promotes a contact angle of the emitted nanobubbles of $0° < \Theta < 90°$.

14. A nanobubbler comprising:
    a porous ceramic material;
    a chamber positioned adjacent to a surface of the porous ceramic material;
    a first inlet configured to inject a gas into the porous ceramic material, wherein the porous ceramic material is configured to emit nanobubbles into the chamber from the surface in response to the injection of the gas;
    a second inlet configured to inject a liquid into the chamber so that the nanobubbles are dislodged from the surface of the porous ceramic material into the liquid; and
    an outlet configured to output from the chamber the liquid infused with the nanobubbles, wherein the surface of the porous ceramic material includes a UV curable epoxy film through which pores have been formed through which the nanobubbles are emitted.

15. The nanobubbler as recited in claim 14, wherein the surface of the UV curable epoxy film is configured so that the emitted nanobubbles have a contact angle of 0°-90°.

16. A nanobubbler comprising:
    a porous ceramic material;
    a chamber positioned adjacent to a surface of the porous ceramic material;
    a first inlet configured to inject a gas into the porous ceramic material, wherein the porous ceramic material is configured to emit nanobubbles into the chamber from the surface in response to the injection of the gas;
    a second inlet configured to inject a liquid into the chamber so that the nanobubbles are dislodged from the surface of the porous ceramic material into the liquid; and
    an outlet configured to output from the chamber the liquid infused with the nanobubbles, wherein the surface of the porous ceramic material is covered by a UV curable epoxy film through which pores have been previously formed through which the nanobubbles are emitted.

17. The nanobubbler as recited in claim 16, wherein the pores formed in the UV curable epoxy film are limited to diameters between 100 nm and 600 nm.

18. A nanobubbler comprising:
    a porous ceramic material;
    a chamber positioned adjacent to a surface of the porous ceramic material;
    a first inlet configured to inject a gas into the porous ceramic material, wherein the porous ceramic material is configured to emit nanobubbles into the chamber from the surface in response to the injection of the gas;
    a second inlet configured to inject a liquid into the chamber so that the nanobubbles are dislodged from the surface of the porous ceramic material into the liquid; and an outlet configured to output from the chamber the liquid infused with the nanobubbles, wherein the porous ceramic material is in a rectangular form having six sides that is configured so that the nanobubbles are emitted only from a first side of the six sides of the porous ceramic material, wherein the other five sides of the porous ceramic material are covered with a film that prevents emission of nanobubbles.

* * * * *